(12) United States Patent
Wittwer (10) Patent No.: US 6,387,621 B1
(45) Date of Patent: *May 14, 2002

(54) AUTOMATED ANALYSIS OF REAL-TIME NUCLEIC ACID AMPLIFICATION

(75) Inventor: Cart T. Wittwer, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/391,811

(22) Filed: Sep. 8, 1999

Related U.S. Application Data (60) Provisional application No. 60/131,256, filed on Apr. 27, 1999.

(51) Int. Cl.[7] .............................. C12Q 1/68; C12P 19/34; G01N 33/48

(52) U.S. Cl. .................. 435/6; 435/91.1; 435/91.2; 435/91.5; 702/19; 702/20

(58) Field of Search .................... 435/6, 91.1, 91.2, 435/91.5; 702/19, 20

(56) References Cited

U.S. PATENT DOCUMENTS

| | | | |
|---|---|---|---|
| 4,592,365 A | * 6/1986 | Georgi | ................. 128/680 |
| 5,455,175 A | 10/1995 | Wittwer et al. | |
| 6,174,670 B1 | * 1/2001 | Wittwer et al. | ............... 435/6 |

FOREIGN PATENT DOCUMENTS

| | | |
|---|---|---|
| WO | WO 97/46707 | 12/1997 |
| WO | WO 97/46712 | 12/1997 |
| WO | WO 97/46714 | 12/1997 |

OTHER PUBLICATIONS

Passing et al, "A new biometrical procedure for testing the equality of measurments from two different analytical methods", J. Clin. Chem. Clin. Biochem. 21:709–720, Nov. 1983.*

Chen et al, "Fluorescence energy transfer detection as a homogenous detection method", Proc. Natl. Acad. Sci. 94:10756–10761, Sep. 1997.*

Ozawa et al, "Quantitative deterimination of deleted mitochondrial DNA relative to normal DNA in parkinsonian striatum by a kinetic PCR analysis", Biochem. Biophys. Res. Comm. 172(2):483–489, Oct. 1990.*

Wittwer, C. T., et al., Continuous Fluorescence Monitoring of Rapid Cycle DNA Amplification, BioTechniques 22, pp. 130–138 (1997).

Higuchi et al., "Kinetic PCR Analysis: Real–Time Monitoring of DNA Amplification Reactions," BioTechnology, vol. 11, pp. 1026–1030 (Sep. 1993).

Ririe et al., "Product Differentiation by Analysis of DNA Melting Curves During the Polymerase Chain Reaction," Analytical Biochemistry 245, pp. 154–160, (1997).

Morrison et al., "Quantification of Low–Copy Transcripts by Continuous SYBR® Green 1 Monitoring During Amplification," BioTechniques, vol. 24, No. 6, pp. 954–962, (1998).

* cited by examiner

*Primary Examiner*—Jeffrey Fredman
(74) *Attorney, Agent, or Firm*—Barnes & Thornburg (57) ABSTRACT

A method is described for analyzing a sample for the presence of a nucleic acid wherein the sample is amplified, illustratively using PCR, in the presence of a fluorescent probe capable of detecting the presence of the nucleic acid sample. A baseline region is determined by comparing the fluorescence at various amplification cycles, and the fluorescence at a selected amplification cycle is compared to the baseline region to determine whether the fluorescence measurement falls outside of that baseline region, indicating the presence of the nucleic acid.

24 Claims, 11 Drawing Sheets

AUTOMATED ANALYSIS OF REAL-TIME NUCLEIC ACID AMPLIFICATION

CROSS-REFERENCE TO RELATED APPLICATION

This application claims priority under 35 U.S.C. §119 (e) to U.S. Provisional Application No. 60/131,256, filed Apr. 27, 1999, which is expressly incorporated by reference herein.

FIELD OF THE INVENTION

The present invention relates to a method of analyzing a sample for the presence of a nucleic acid. More particularly, the present invention is directed to an automated method for detecting and reporting the presence of a predetermined nucleic acid in a sample using polymerase chain reaction and a fluorescent detecting entity.

BACKGROUND AND SUMMARY OF THE INVENTION

Amplification of DNA by polymerase chain reaction (PCR) is a technique fundamental to molecular biology. Nucleic acid analysis by PCR requires sample preparation, amplification, and product analysis. Although these steps are usually performed sequentially, amplification and analysis can occur simultaneously. DNA dyes or fluorescent probes can be added to the PCR mixture before amplification and used to analyze PCR products during amplification. Sample analysis occurs concurrently with amplification in the same tube within the same instrument. This combined approach decreases sample handling, saves time, and greatly reduces the risk of product contamination for subsequent reactions, as there is no need to remove the samples from their closed containers for further analysis. The concept of combining amplification with product analysis has become known as "real time" PCR. See, for example, WO/9746707A2, WO/9746712A2, WO/9746714A1, all published Dec. 11, 1997, incorporated herein by reference.

Monitoring fluorescence each cycle of PCR initially involved the use of ethidium bromide. Higuchi R, G Dollinger, P S Walsh and R. Griffith, Simultaneous amplification and detection of specific DNA sequences, Bio/Technology 10:413–417, 1992; Higuchi R, C Fockler G Dollinger and R Watson, Kinetic PCR analysis: real time monitoring of DNA amplification reactions, Bio/Technology 11:1026–1030, 1993. In that system fluorescence is measured once per cycle as a relative measure of product concentration. Ethidium bromide detects double stranded DNA; if template is present fluorescence intensity increases with temperature cycling. Furthermore, the cycle number where an increase in fluorescence is first detected increases inversely proportionally to the log of the initial template concentration. Other fluorescent systems have been developed that are capable of providing additional data concerning the nucleic acid concentration and sequence.

While PCR is an invaluable molecular biology tool, the practical implementation of real time PCR techniques has lagged behind the conceptual promise. Currently available instrumentation does not actually analyze data during PCR; it simply acquires the data for later analysis. After PCR has been completed, multiple manual steps are necessary to analyze the acquired data, and human judgment is typically required to provide the analysis result. What is needed is a system for automating data acquisition and analysis so that no user intervention is required for reporting the analytical results. Thus, when the temperature cycling in a polymerase chain reaction amplification is complete, the system software is automatically triggered and the results, for example, the presence or absence of a given pathogen, is immediately displayed on screen. Algorithms for detection, quantification, and genotyping are needed. Moreover, initiation of the analysis algorithm can be implemented prior to completion of temperature cycling. Data processing can occur during amplification and concomitant analysis results can be used to modify temperature cycling and to acquire additional data during the latter stages of the amplification procedure to optimize amplification protocol and data quality.

A major problem in automating PCR data analysis is identification of baseline fluorescence. Background fluorescence varies from reaction to reaction. Moreover, baseline drift, wherein fluorescence increases or decreases without relation to amplification of nucleic acids in the sample, is a common occurrence. Prior attempts to automate amplification data analysis involved setting the baseline fluorescence as that measured at one or more predetermined early cycle numbers. This technique accounts for the variation in background fluorescence, but it does not compensate for baseline drift. Without compensation for baseline drift, automated amplification data analysis can easily provide both false negative and false positive results.

Thus, one aspect of the present invention is directed to a method of determining the presence of a nucleic acid in a sample by using a fluorescent entity capable of detecting the nucleic acid and amplifying the nucleic acid in the presence of the fluorescent entity. A baseline fluorescence region is determined by analyzing the fluorescence measurements of a number of amplification cycles, and the fluorescence measurements during specific amplification cycles are compared to the baseline fluorescence region to determine the presence or absence of the nucleic acid. In a preferred embodiment, the baseline fluorescence region is determined by calculating the slope of a fluorescence intensity verses amplification cycle plot at each of the amplification cycles and choosing the fluorescence measurement of the amplification cycle with the slope having an absolute value closest to zero. Preferably, the baseline fluorescence region is generated as the square root of the mean square error.

In another embodiment, the baseline fluorescence region is determined and the fluorescence values are compared thereto after each amplification cycle. Thus, the presence of the nucleic acid sequence can be determined more quickly in samples containing higher copy number. Furthermore, the remaining cycles may be used to acquire other information concerning the nucleic acid sample, such as initial copy number and allelic data.

In an additional embodiment, the process is automated so that a user can prepare a biological sample and simply place it in a thermal cycler having a sensor for reporting fluorescence values as a function of cycle number and a processor programmed with an algorithm capable of processing the values and reporting a positive or negative result.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIGS. 1a–l show a comparison of three fluorescence monitoring schemes, (FIGS. 1a, d, g, j) dsDNA dye, (FIGS.

1*b, e, h, k*) exonuclease probe, and (FIGS. 1*c, f, i, l*) hybridization probe, for PCR amplification, wherein each scheme is illustrated (FIGS. 1*a–c*) before amplification and (FIGS. 1*d–f*) after amplification, and fluorescence values are shown (FIGS. 1*g–i*) once during each cycle of PCR and (FIGS. 1*j–l*) continuously during PCR.

FIGS. 7 and 8 illustrate positive results, while FIGS. 9–11 illustrate negative results.

DETAILED DESCRIPTION OF THE INVENTION

In describing and claiming the invention, the following terminology will be used in accordance with the definitions set forth below.

As used herein, "nucleic acid," "DNA," and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

As used herein, "fluorescence resonance energy transfer pair" or "FRET pair" refers to a pair of fluorophores comprising a donor fluorophore and acceptor fluorophore, wherein the donor fluorophore is capable of transferring resonance energy to the acceptor fluorophore. In other words the emission spectrum of the donor fluorophore overlaps the absorption spectrum of the acceptor fluorophore. In preferred fluorescence resonance energy transfer pairs, the absorption spectrum of the donor fluorophore does not substantially overlap the absorption spectrum of the acceptor fluorophore.

As used herein, "FRET oligonucleotide pair" refers to a pair of oligonucleotides, each labeled with a member of a fluorescent resonance energy transfer pair, wherein hybridization to complementary target nucleic acid sequences brings the fluorescent entities into a fluorescence resonance energy transfer relationship.

The present invention is directed to a method of analyzing a sample for the presence of a nucleic acid wherein the sample is amplified, preferably using PCR, in the presence of a fluorescent probe capable of detecting the presence of the nucleic acid sample. A baseline region is determined by comparing the fluorescence at various amplification cycles, and the fluorescence at each of various amplification cycles is compared to the baseline region to determine whether the fluorescence measurements fall outside of that baseline region.

Many different probes have recently become available for monitoring PCR. Although not sequence specific, double stranded DNA (dsDNA) specific dyes can be used in any amplification without the need for probe synthesis. Such dyes include ethidium bromide and SYBR™ Green I. With dsDNA dyes, product specificity can be increased by analysis of melting curves or by acquiring fluorescence at a high temperature where nonspecific products have melted. Ririe K M, Rasmussen R P and C T Wittwer, Product differentiation by analysis of DNA melting curves during the polymerase chain reaction, Anal. Biochem. 245-154–160, 1997; Morrison T B, J&J Weis and C T Wittwer, Quantification of low copy transcripts by continuous SYBR Green I monitoring during amplification, BioTechniques 24:954–962, 1998.

Oligonucleotide probes can also be covalently labeled with fluorescent molecules. Hairpin primers (Sunrise™ primers), hairpin probes (Molecular Beacons™) and exonuclease probes (TaqMan™) are dual-labeled oligonucleotides that can be monitored during PCR. These probes depend on fluorescence quenching of a fluorophore by a quencher on the same oligonucleotide. Fluorescence increases when hybridization or exonuclease hydrolysis occurs.

A preferred design employs two oligonucleotides, each labeled with a fluorescent probe. Hybridization of these oligonucleotides to a target nucleic acid brings the two fluorescent probes close together to allow resonance energy transfer to occur. Wittwer C T, M G Herrmann, A A Moss and R P Rasmussen, Continuous fluorescence monitoring 6f rapid cycle DNA amplification, BioTechniques 22:130–138, 1997. These hybridization probes require only a single fluorescent label per probe and are easier to design and synthesize than dual labeled probes. Acceptable fluorophore pairs for use as fluorescent resonance energy transfer pairs are well known to those skilled in the art and include, but are not limited to, fluorescein/rhodamine, phycoerythrin/Cy7, fluorescein/Cy5, fluorescein/Cy5.5, fluorescein/LC Red 640, and fluorescein/LC Red 705.

Figure 1A:
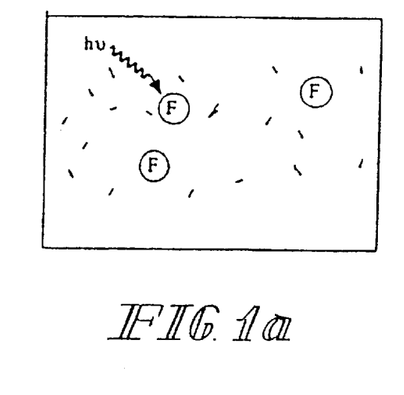
Figure 1B:
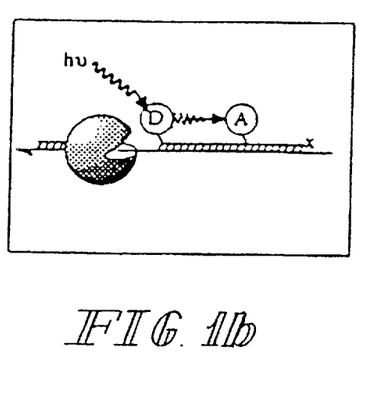
Figure 1C:
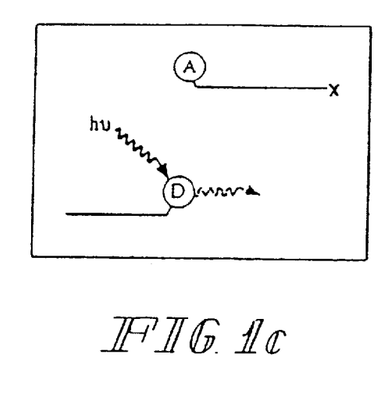
Figure 1D:
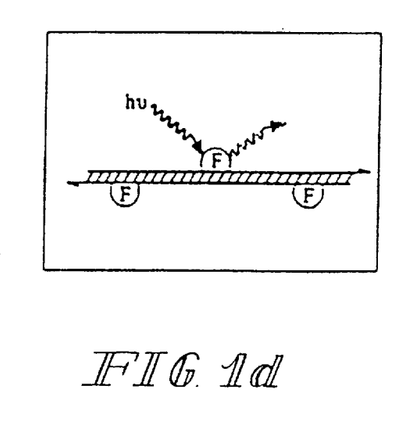
Figure 1E:
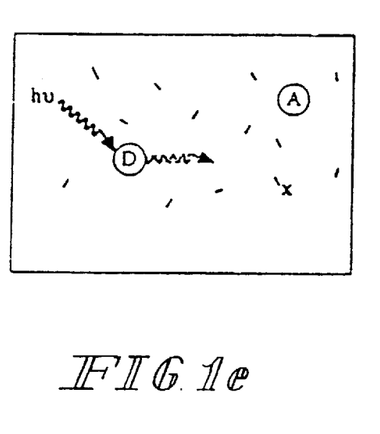
Figure 1F:
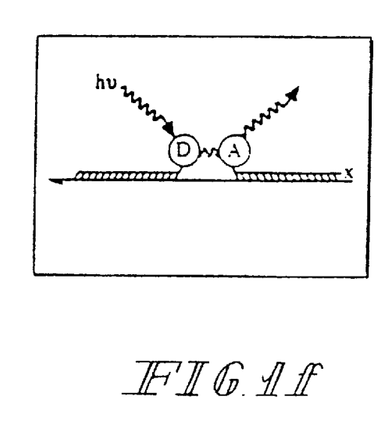
Figure 1G:
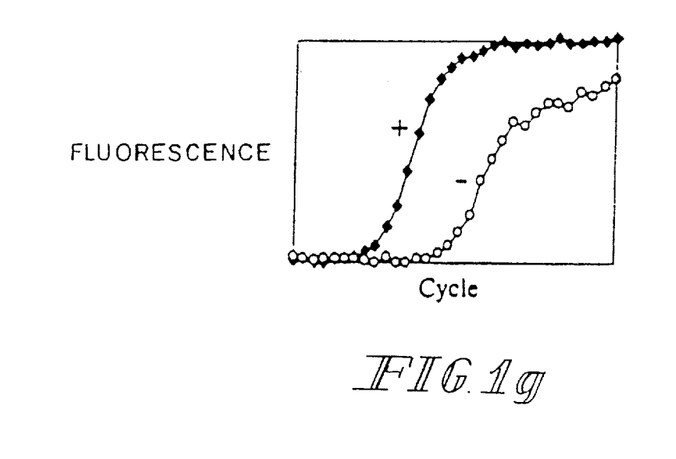
Figure 1H:
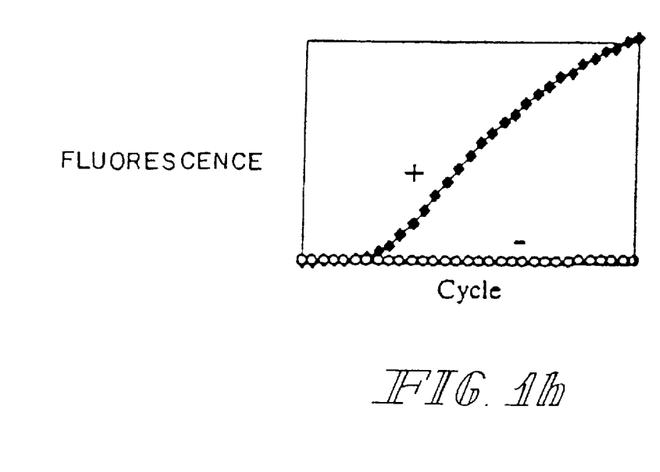
Figure 1I:
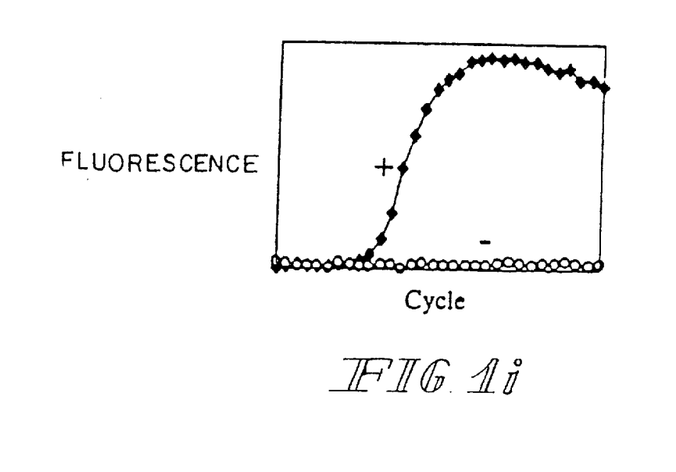
Figure 1J:
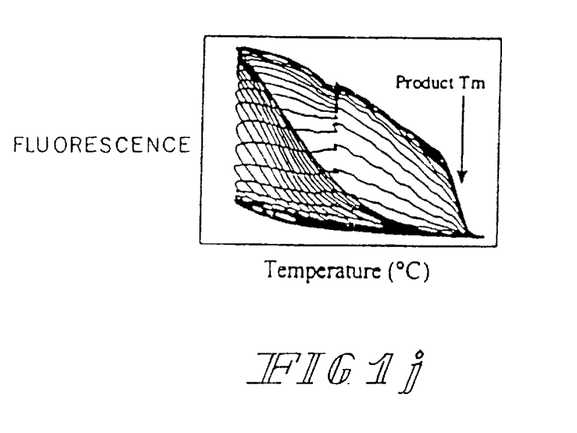
Figure 1K:
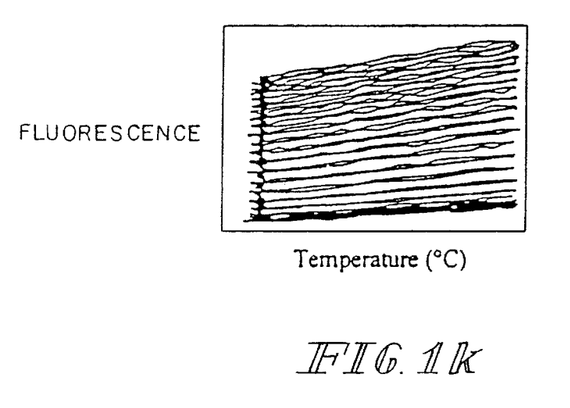
Figure 1L:
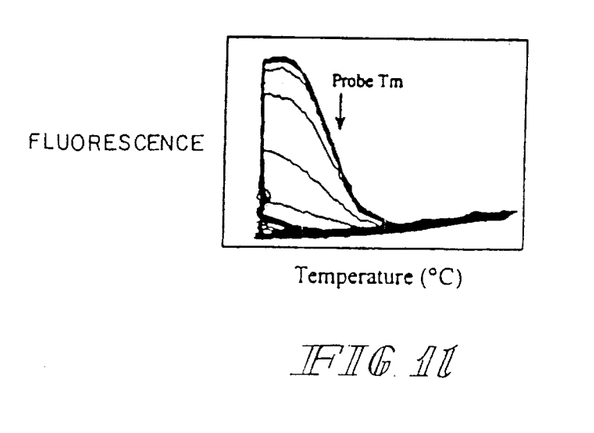

SYBR™ Green I, exonuclease probe and hybridization probe designs are shown in FIGS. 1*a–l* For each design, schematics both before (FIGS. 1*a–c*) and after (FIGS. 1*d–f*) amplification are shown, as well as cycle verses fluorescence amplification plots of positive and negative controls (FIGS. 1*g–i*), and temperature verses fluorescence plots from continuous monitoring (FIGS. 1*j–l*). SYBR Green I fluorescence increases as more dsDNA is made (FIGS. 1*a, d, g, j*). A Because the dye is not sequence specific, a negative control also increases in fluorescence during later cycles as primer dimers are formed. In FIGS. 1*b, e, h, k*, dual-labeled fluorescein/rhodamine probes are cleaved during polymerase extension by 5'-exonuclease activity, separating the fluorophores and increasing the fluorescein emission. The signal generated is cumulative and the fluorescence continues to increase even after the amount of product has reached a plateau. FIGS. 1*c, f, i, l* shows use of a FRET oligonucleotide pair wherein two probes hybridize next to each other, one labeled 3' with fluorescein and the other labeled 5' with Cy5. As product accumulates during PCR, fluorescence energy transfer to Cy5 increases. The fluorescence of hybridization probes decreases at high cycle number because of probe/product competition.

Standard instruments for PCR complete 30 cycles in about two to four hours. A preferred system is a rapid thermal cycling device using capillary tubes and hot air temperature control. See, for example, U.S. Pat. No. 5,455,175, herein incorporated by reference. Because of the low heat capacity of air and the thin walls and high surface area of capillary tubes, small volume samples could be cycled quickly. The total amplification time for 30 cycles is reduced to 15 minutes with excellent results.

The use of capillaries with forced air heating allows precise control of sample temperature at a speed not possible with other designs. For example, sample temperature verses time plots in capillaries show sharp spikes at denaturation and annealing temperatures, whereas several seconds are required for all of the sample to reach equilibrium in conical plastic tubes. Wittwer, C T, G B Reed and K M Ririe, Rapid cycle DNA amplification, in K Mullis, F Ferre, and R Gibbs (Eds.), The polymerase chain reaction, Springer-Verlag, Deerfield Beach, Fla. pp. 174–181, 1994; Wittwer, C T, B C Marshall, G B Reed, and J L Cherry, Rapid cycle allele-specific amplification: studies with the cystic fibrosis delta F508 locus, Clin. Chem., 39:804–809, 1993. Rapid temperature cycling with minimal annealing and denaturation times improves quantitative PCR and increases the discrimination of allele specific amplification. Weis, J H, S S Tan, B K Martin, and C T Wittwer, Detection of rare mRNA species via quantitative RT-PCR, Trends in Genetics, 8:263–4, 1992; Tan S T and J H Weis, Development of a sensitive reverse transcriptase PCR assay, RT-RPCR, utilizing rapid cycle times, PCR Meth. and Appl. 2:137–143, 1992. Rapid cycling for cycle sequencing reduces sequencing artifacts and minimizes "shadow banding" in dinucleotide repeat amplifications. Swerdlow H, K Dew-Jager and R F Gesteland, Rapid cycle sequencing in an air thermal cycler, BioTechniques 15:512–519, 1993; Odelberg S J and R White, A method for accurate amplification of polymorphic CA-repeat sequences, PCR Meth. Appl. 3:7–12, 1993. For long PCR, yield is improved when the sample is exposed as little as possible to high denaturation temperatures. Gustafson C E, R A Alm and T J Trust, Effect of heat denaturation of target DNA on the PCR amplification. Gene 23:241–244, 1993. The RapidCycler™, developed by Idaho Technology, is an example of a rapid thermal cycling device. The LightCycle ™ is a rapid temperature cycler with a fluorimeter, wherein light emitting diodes are used for excitation and photodiodes are used for detection.

The present invention is directed to methods for automating detection nucleic acids with real time PCR. While these algorithms may be applied to any amplification system, it is preferred to integrate these algorithms into the LightCycler™ platform. These analysis routines are triggered by the completion of rapid thermal cycling for "hands off" amplification, analysis, and final results presentation in a total of less than 15 min. The analysis routines take from <1 second for detection and quantification to <10 seconds for genotyping. LabView (National Instruments, Austin, Tex.), a graphical programming language, is preferred for LightCycler™ instrument control. The LightCycle ™ is a PC-based instrument.

Perhaps the most basic analysis of real time PCR data is a judgement of whether a targeted nucleic acid is present. If the nucleic acid is present, further quantification and genotyping may take place. In many cases, a yes/no judgement is all that is needed. For example, one may want to determine whether *E. coli* 0157:H7 is in a sample of hamburger, whether anthrax is on a swab from a soldier; or whether hepatitis C is in a unit of blood. Real time PCR can improve yes/no detection over end point PCR assays because fluorescence is acquired at each cycle.

Figure 2:
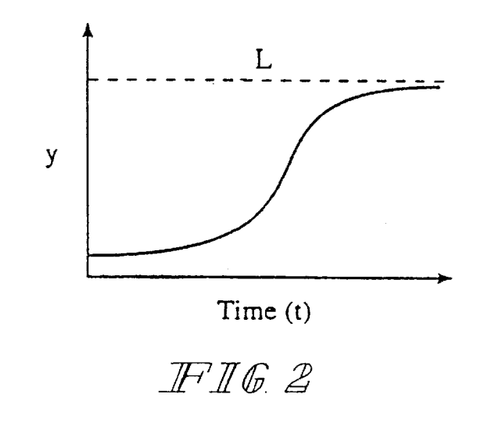
FIG. 2 is a graph illustrating logistic growth.

Inspection of cycle verses fluorescence data from positive and negative real time PCR runs (see FIGS. 1h and 1i) suggests that discrimination is simple. The positive samples increase with cycle number while the negative samples remain at baseline. A trained observer expects positive samples to follow an S-shape curve, beginning with a baseline, followed by an exponential segment, and finishing with a plateau. The expected curve is similar to the logistic model for population growth, where the rate of growth is proportional to both the population size y and to the difference L–y, where L is the maximum population that can be supported. For small y, growth is exponential, but as y nears L the growth rate approaches zero. An example of logistic growth is shown in FIG. 2.

Although intuitively simple, accurately discriminating between positive and negative samples is not easy in practice. The simplest approach is to set a horizontal fluorescence threshold as a discriminator between positive and negative samples. This works best with a stable baseline (between and within samples) and a known fluorescence intensity that correlates with "positive." Although this method will work on obvious samples (e.g. FIGS. 1h and 1i), a more robust algorithm is desired that will work under a wider variety of conditions. For example, the baseline may drift and the fluorescence intensity may vary greatly between different samples and probe techniques. Thus, the present invention is directed to a method that will: (1) automatically identify the baseline, (2) use the baseline variance to establish a confidence region, and (3) call each sample positive or negative based on the relationship of the confidence region to the fluorescence data.

Figure 3A:
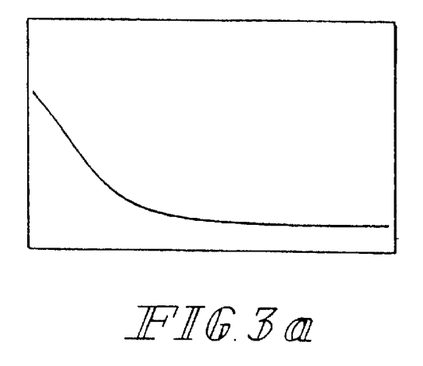
FIGS. 3*a–f* show a comparison of various cycle-verses-fluorescence curve types.
Figure 3B:
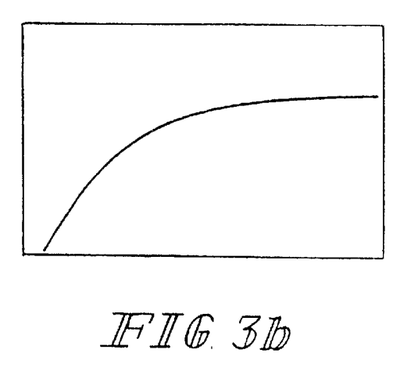
Figure 3C:
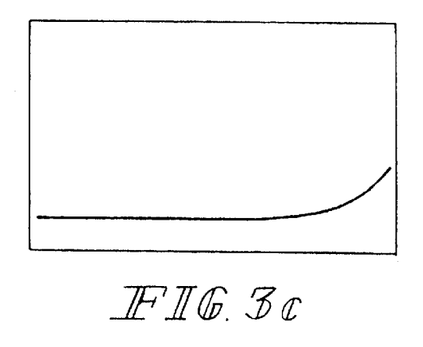
Figure 3D:
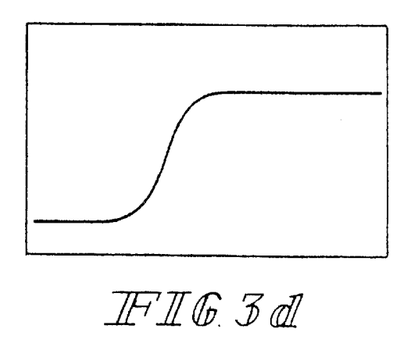
Figure 3E:
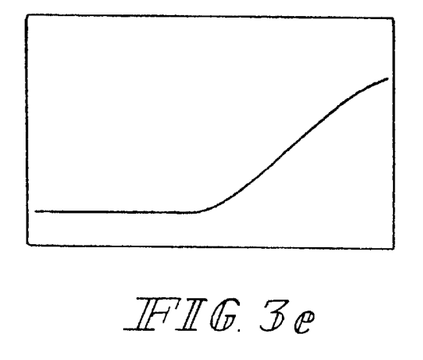

FIGS. 3a–f display various types of amplification curves, all of which have been observed in LightCycler™ runs. FIGS. 3A and B show curves from samples that are negative with no template present. The fluorescence scales in FIGS. 3A and B are magnified (compared to FIGS. 3C–F) to demonstrate the baseline drift and to provide algorithms capable of being independent of the fluorescence intensity. There is always some baseline drift during cycling. This drift usually is greatest at the beginning of cycling but later levels off, and may be either downward (FIG. 3A) or upward (FIG. 3B). This baseline drift of negative reactions must be distinguished from positive reactions of either low copy numbers (FIG. 3C) or high copy numbers (FIG. 3D) of starting template. The method needs to work with various probe designs, including exonuclease (FIG. 3E) and hybridization (FIG. 3F) probes.

Automatic identification of the background is surprisingly difficult. In prior art methods, the baseline is determined as a function of measured fluorescence at a fixed range of cycles near the beginning of amplification. However, selection of a fixed range of cycles is not adequate because both downward drift (FIG. 3A) and high copy (FIG. 3D) amplifications may be incorrectly called.

Figure 4:
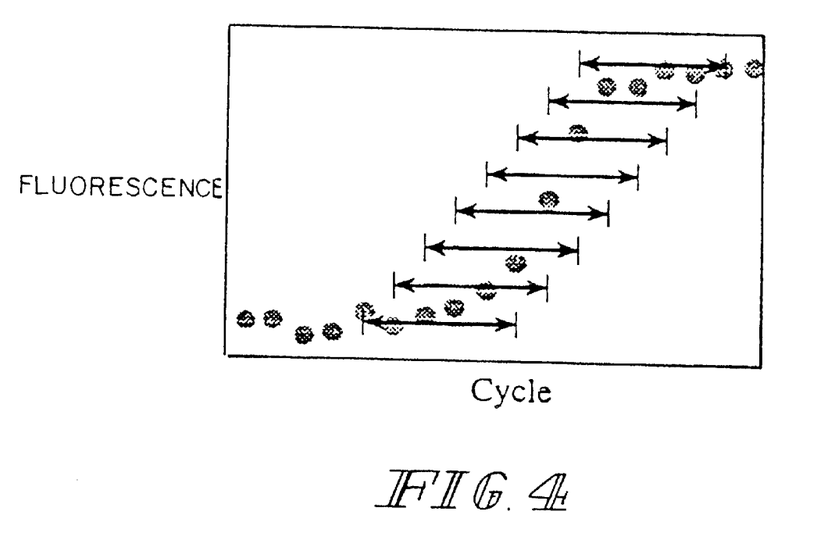
FIG. 4 illustrates a sliding window analysis for determining the slope of the fluorescence-verses-cycle number graph at each cycle.
Figure 5:
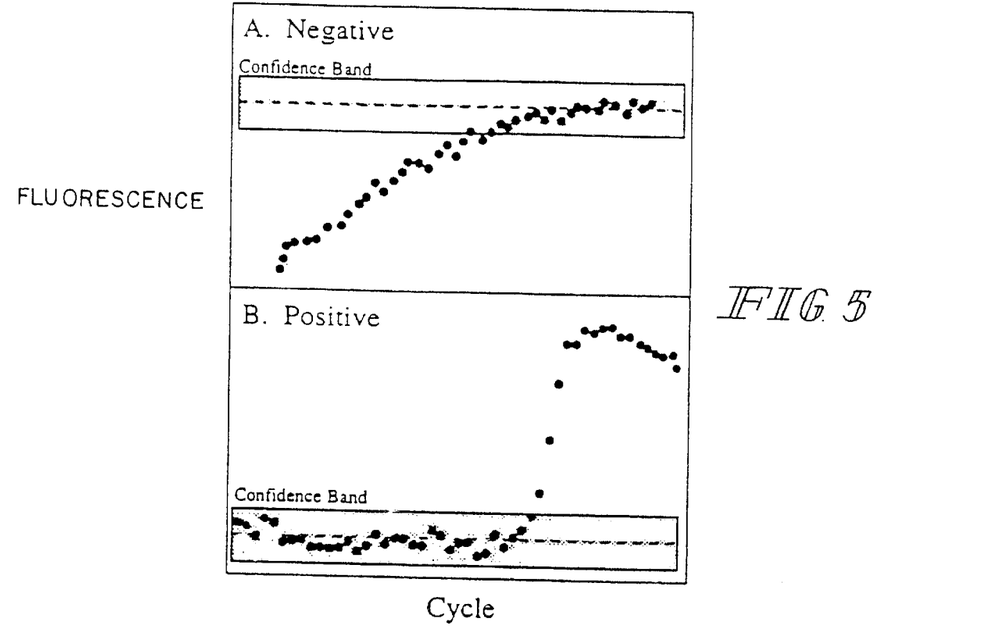
FIG. 5 shows typical fluorescence verses amplification cycle graphs for (A) a negative sample and (B) a positive sample.

In the present invention, the background is identified by analyzing the fluorescent measurements over a wide range of amplification cycles. Preferably, the background is identified by selecting the sliding window (FIG. 4) with the shallowest slope. That is, calculate the slope at each cycle by linear regression of the local neighborhood (for example, a 7 point sliding window). The window with the slope of lowest absolute value (least difference from zero) defines the background region. Once the background region has been identified the variation of these background points about their regression line (the square root of the mean square error) is multiplied by a constant to determine a confidence band. This confidence band will have a slope near zero and is extrapolated across all cycles. If the fluorescence of the last cycle is within the confidence band it is negative, if it is outside the band it is positive. FIG. 5 demonstrates both cases.

Figure 6:
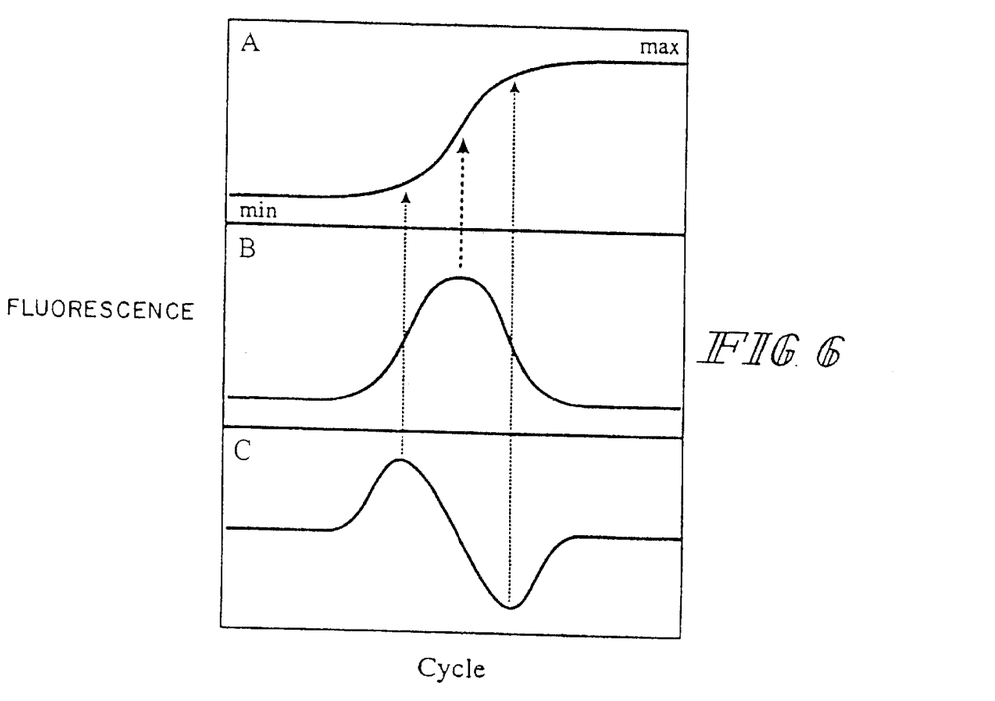
FIG. 6 also shows typical amplification graphs wherein (A) shows fluorescence verses amplification cycle, (B) is the first derivative of fluorescence verses amplification cycle, and (C) is the second derivative of fluorescence verses amplification cycle.

This algorithm should work well in most cases. However, with the high copy fluorescence curve type (FIG. 3D), the shallowest slope might be found at early cycles (resulting in a correct positive call) or at late cycles (resulting in an incorrect negative call). This exception may be handled by analyzing the curve shape. In a well-behaved amplification, the expected amplification curve shape is ordered by cycle number as follows:

1. Minimum fluorescence
2. Maximum second derivative (F")
3. Maximum first derivative (F')
4. Minimum second derivative (F")
5. Maximum fluorescence This gives the characteristic S-curve shape we expect during PCR (FIG. 6A). The maximum slope (first derivative) is obtained from the sliding window analysis already performed for background identification. Preferably, the second derivatives are calculated by a 3-point sliding window linear regression of the first derivatives. If the curve shape is well behaved (that is, if looking at a graph of FIG. 6, and reading from lowest to highest cycle number, the features occur in the order listed above), then the background is only selected from sliding windows centered at cycle numbers less than the second derivative maximum. This solves the potential analysis problem with FIG. 3D. In other preferred embodiments, cycle numbers less than the first derivative maximum or cycle numbers less than the second derivative minimum may be used. It will be further understood that any cycle number between the second derivative maximum and the second derivative minimum is a suitable cutoff cycle for use with this technique and is within the scope of this invention.

Figure 3F:
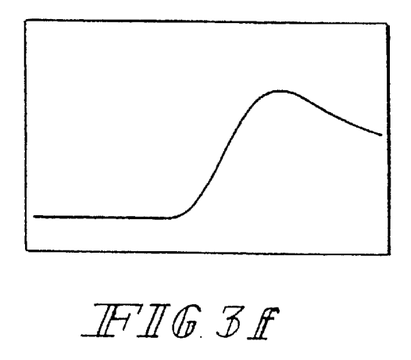

Another method is to compare the cycle with the greatest fluorescence (which is not necessarily the last cycle) to the confidence band. This is especially suited for hybridization probes that may decrease in fluorescence with extensive cycling, such as seen in FIG. 3F. The cycle with the greatest fluorescence only should be used when the curve shape is well behaved, in order to prevent false positive calls with downward drifts, such as shown in FIG. 3A.

The variables to optimize for automatic detection are: 1) the window size for the first derivative estimate, 2) the window size for the second derivative estimate, and 3) the confidence band factor. A reasonable value for the first derivative window size is 7, although 3, 5, 9, and 11 are also quite useful. For the second derivative the preferred window size is 3, but 5, and 7 have also proven to be useful values. A preferred confidence band factor is 20. As the first derivative window size increases the variance estimate is more accurate, but the edge cycles (beginning and ending) are lost.

This algorithm is best understood by referring to the fluorescence verses cycle test result plot shown in FIGS. 7–11. The input data consist of one fluorescence value for each cycle of amplification, shown as the closed white circles. Let this equal array Yi, where i is the cycle number and N is the total number of cycles. The detection criteria are:

A=the number of fluorescence values used to determine the first derivatives. It is convenient to use odd numbers, so that the first derivatives correspond to integer cycle numbers. As discussed above, reasonable values include 3, 5, 7, 9, and 11. Preferably, 7 is used as the first derivative window size.

B=the number of first derivative values used to determine the second derivatives. Again, it is convenient to use odd numbers, so that the second derivative values also correspond to integer cycle numbers. Reasonable values include 3, 5, and 7, with 3 being the preferred value.

C=the confidence band factor. This factor determines the confidence band by multiplying it by a variance measure, preferably the square root of the mean square error.

Figure 7:
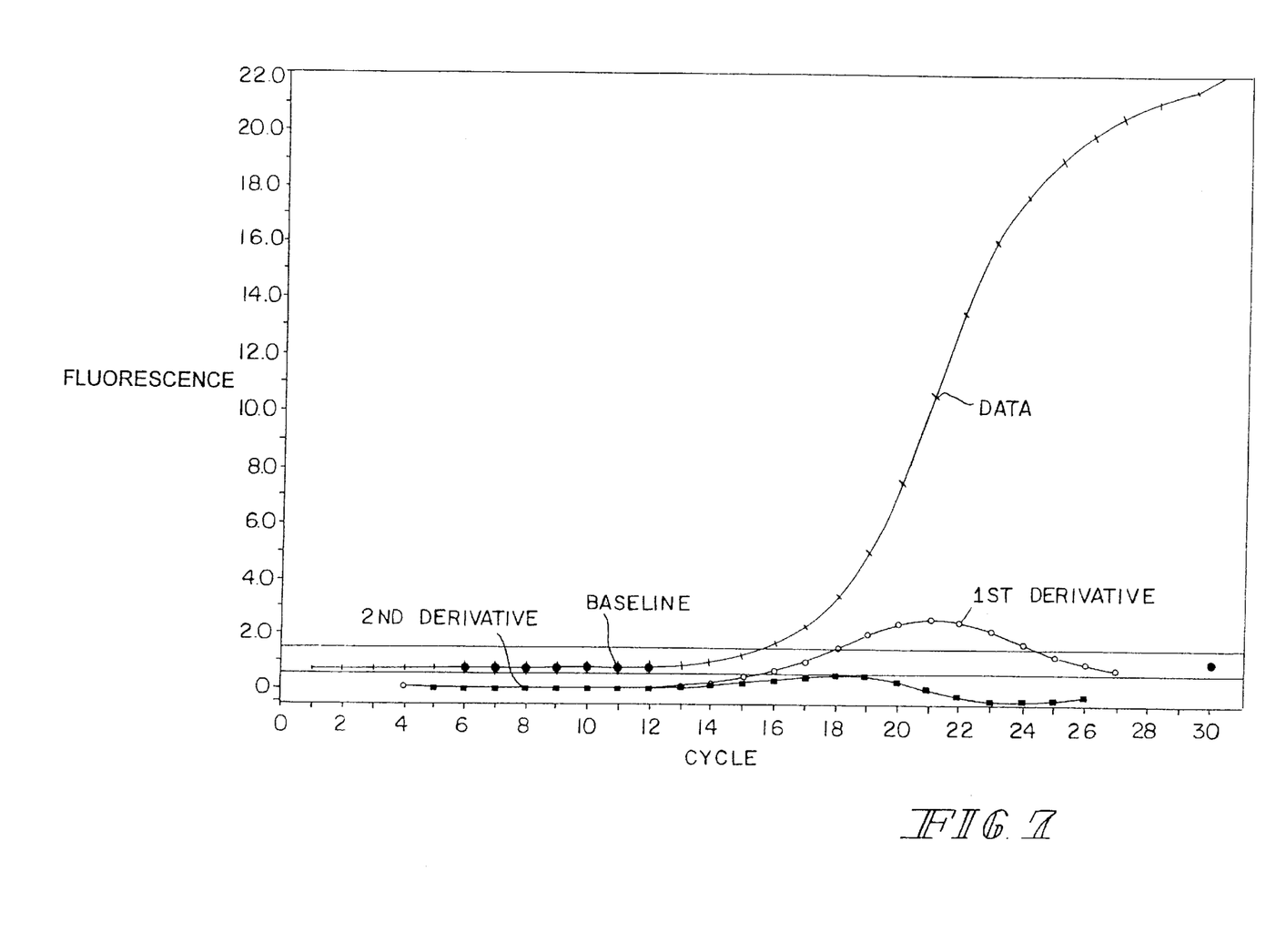
FIGS. 7–11 show the results for various samples wherein open white circles represent the fluorescence measurement at each cycle, open black circles represent the first derivatives, closed black circles represent second derivatives, large black circles connected by lines represent the points contributing to the baseline calculation, and the horizontal lines illustrate the baseline region.

The first step is to calculate the first and second derivatives. Although there are many ways to accomplish this, a preferred method is to determine the first derivatives as the slope of a linear regression line through A points, and assigning the value to the central cycle number. Some cycles on either edge cannot be assigned first derivatives, but first derivatives can be provided for cycles $(A+1)/2$ through $N-(A-1)/2$. Similarly, the second derivatives are calculated as the slope of the first derivative points and assigned to cycles $(A+1)/2+(B-1)/2$ through $[N-(A-1)/2]-(B-1)/2$. Calculation of the first and second derivatives provide arrays Y'i and Y"i, with some edge values missing. In FIG. 7, the first and second derivatives are displayed as open black circles and closed black circles, respectively.

The next step is to determine whether the fluorescence curve has a well-behaved shape. As discussed above, the well-behaved shape occurs when the cycles with minimum fluorescence, maximum second derivative, maximum first derivative, minimum second derivative, and maximum fluorescence occur in that order, from low to high cycle number.

The baseline is then determined. If the fluorescence curve does not have the expected shape, the cycle whose first derivative is closest to zero is used. If the fluorescence curve has a well-behaved shape, the cycle whose first derivative is closest to zero chosen from among all cycles prior to the cycle with the maximum second derivative (again, any cycle between the maximum second derivative and the minimum second derivative may also be used as the cutoff cycle number). The baseline is drawn through the fluorescence value of the chosen cycle with a slope of its first derivative. In FIG. 7, the A points contributing to the first derivative calculation for the baseline are displayed as large black dots connected by a line.

The next step is to determine the test point cycle, that is, the cycle used to compare against the baseline for determining a positive or negative result. If the curve is not well-behaved, the test point is the last cycle. If the fluorescence curve is well-behaved, the test point is the cycle with fluorescence farthest from the baseline. The test point fluorescence of a negative sample can be predicted as the intersection of the baseline with the test point cycle.

Next, a confidence interval can be determined about the predicted negative test point. Preferably, this is done by finding the square root of the mean square error about the baseline of A points used to determine the baseline. This is multiplied by C. The product is added to the predicted negative test point to get the upper fluorescence limit of the confidence interval and is subtracted from the predicted negative test point to get the lower limit of the confidence interval. These limits are shown on FIG. 7 as two solid horizontal lines.

Figure 8:
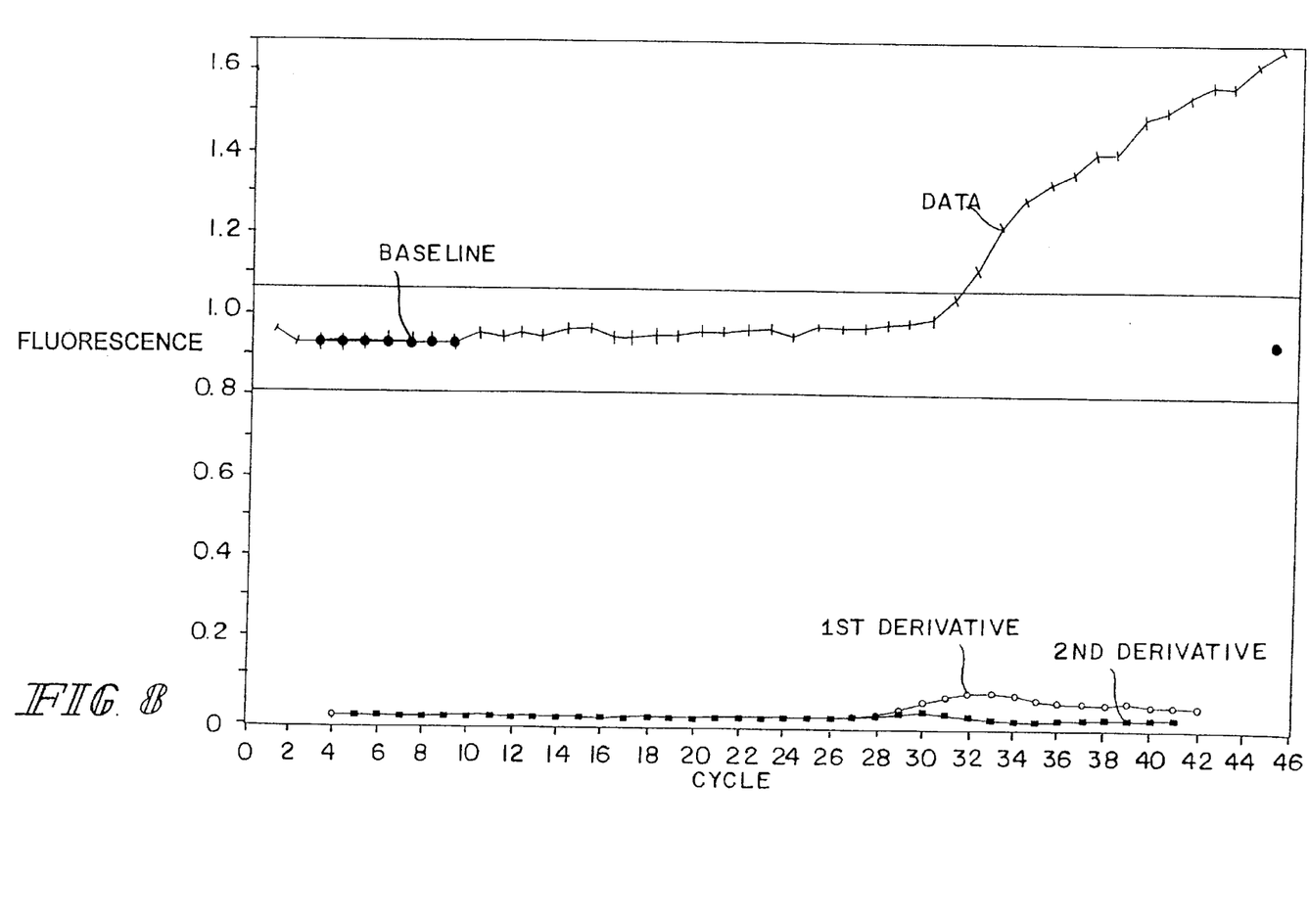
Figure 9:
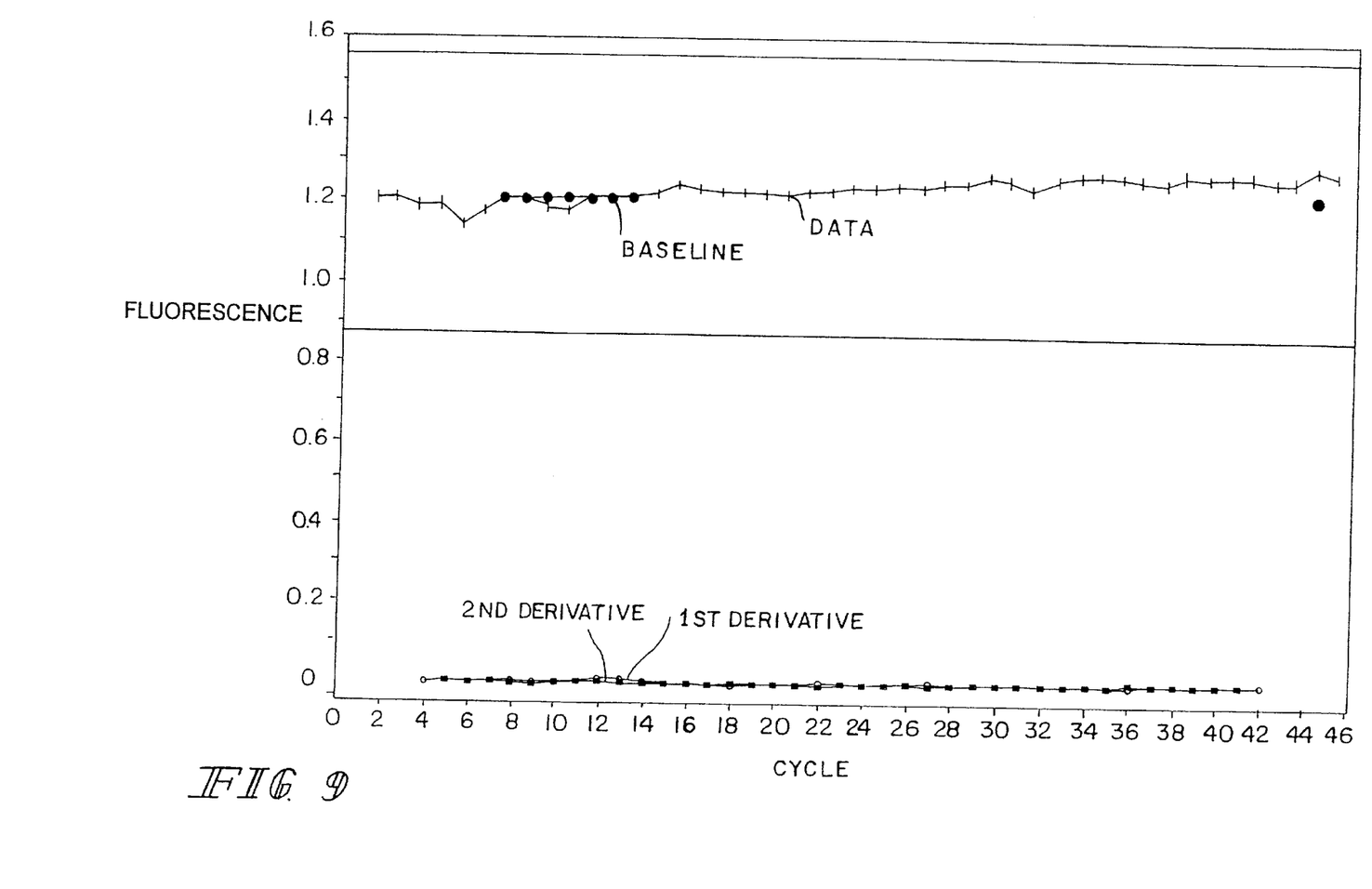
Figure 10:
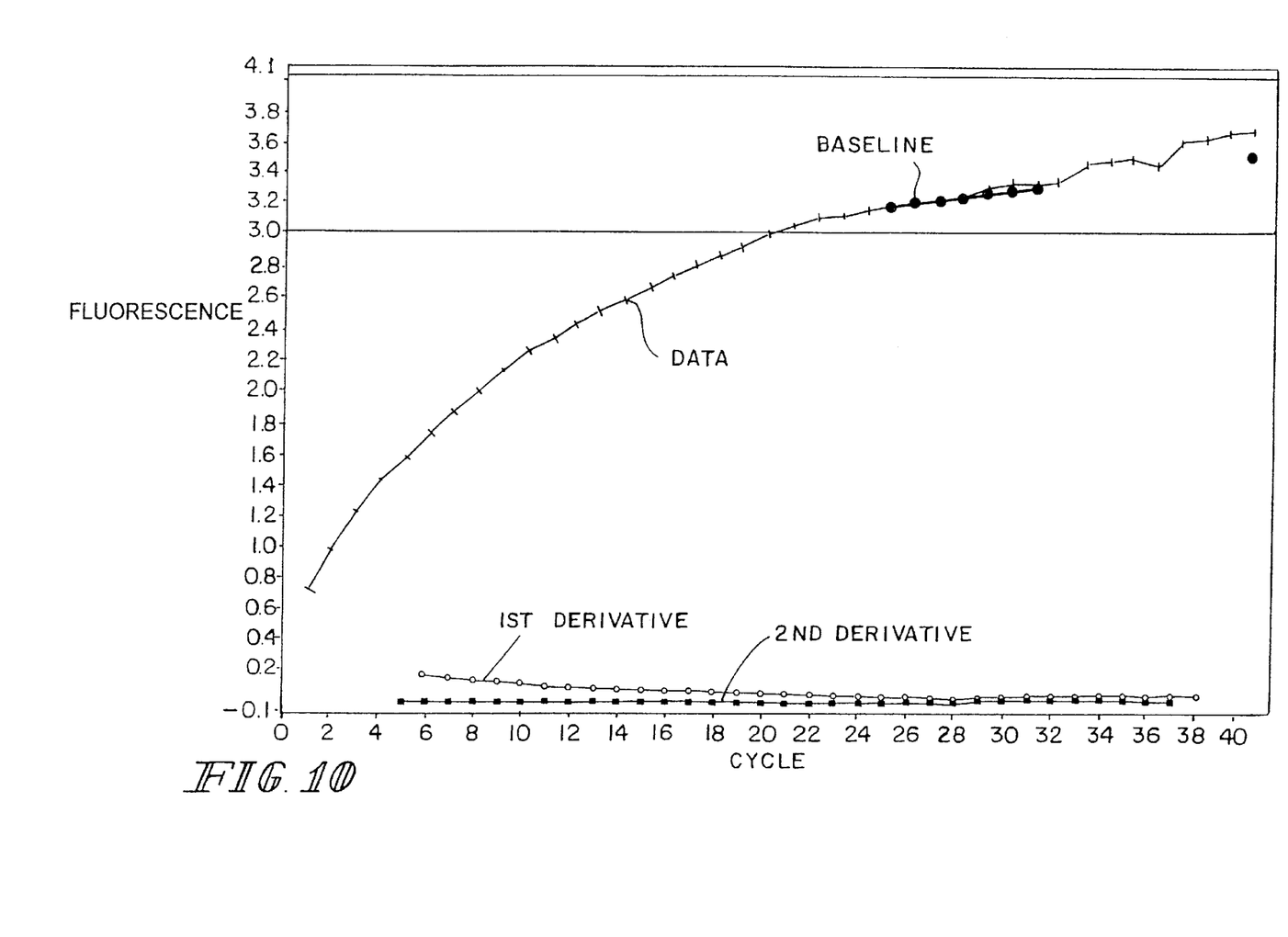
Figure 11:
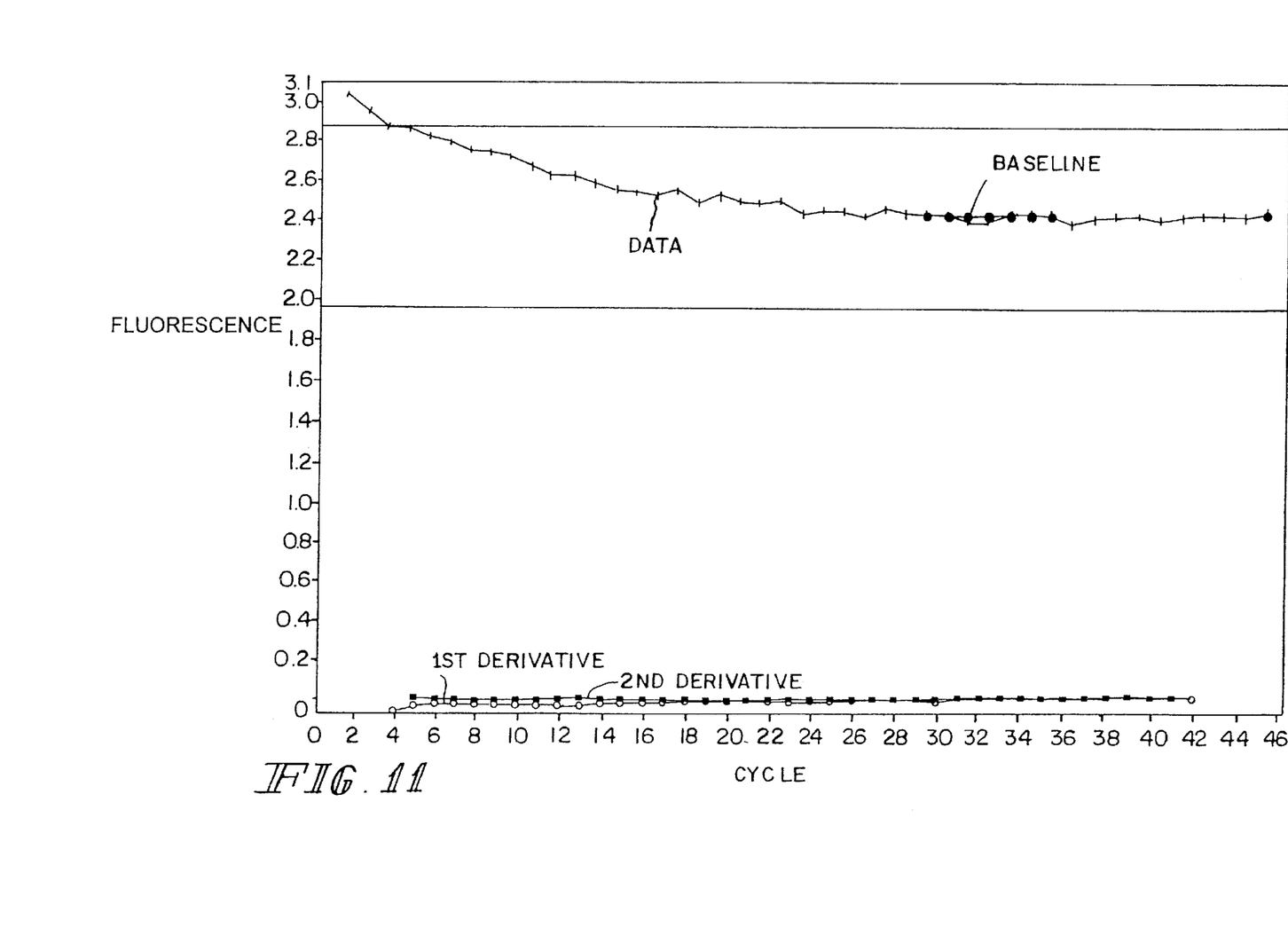

The final step is to declare the sample positive or negative. If the test point fluorescence is outside of the confidence interval, the sample is positive. If it is within the interval, the sample is negative. FIGS. 7 and 8 are samples which are positive, while FIGS. 9–11 are negative samples.

Although the invention has been described in detail with reference to preferred embodiments, variations and modifications exist within the scope and spirit of the invention as described and defined in the following claims.

What is claimed is:

1. A method for determining the presence of a nucleic acid comprising the steps of providing a fluorescent entity capable of indicating the presence of the nucleic acid and capable of providing a signal related to the quantity of the nucleic acid, amplifying the nucleic acid through a plurality of amplification cycles in the presence of the fluorescent entity, measuring fluorescence intensity of the fluorescent entity at each of the plurality of amplification cycles to produce a fluorescent value for each cycle related to the quantity of the nucleic acid present at each cycle, generating a fluorescence-verses-amplification-cycle plot wherein the fluorescent values are recorded for each amplification cycle, calculating slopes of segments of the fluorescence-verses-amplification-cycle plot using a plurality of the fluorescent values, using the segment slopes of the fluorescence-verses-amplification-cycle plot to establish a baseline fluorescence region by generating a slope value for each of a plurality of the amplification cycles, and establishing the baseline fluorescence region comprising an interval of cycles that includes the amplification cycle with the slope value having an absolute value closest to zero, and ascertaining whether the fluorescence value during a selected amplification cycle is outside the baseline fluorescence region.

2. The method of claim 1 wherein the segment slopes are calculated by linear regression of each local neighborhood.

3. The method of claim 1 wherein the amplification cycle with the slope value having the absolute value closest to zero comprises a central cycle of the interval of cycles used to establish the baseline fluorescence region.

4. The method of claim 1 wherein the baseline fluorescence region is centered on a line passing through the measured fluorescence of the amplification cycle with the slope value having the absolute value closest to zero, the line having a slope equal to the slope value having the absolute value closest to zero, and the baseline fluorescence region including an area on at least one side of the line defined by a variance measure of the fluorescence values.

5. The method of claim 4 wherein the variance measure is calculated from the amplification cycles used in establishing the baseline fluorescence region.

6. The method of claim 1 wherein the fluorescent entity comprises a FRET oligonucleotide pair.

7. The method of claim 1 wherein the fluorescence-verses-amplification-cycle plot is a well-behaved amplification curve, and further comprising the steps of determining the cycle having the maximum measured fluorescence, and determining whether the maximum fluorescence is above the baseline fluorescence region.

8. The method of claim 1 wherein the fluorescence-verses-amplification-cycle plot is an amplification curve which is not well behaved, and determining if the fluorescence of a last cycle tested is outside the baseline fluorescence region.

9. A method for determining the presence of a nucleic acid comprising the steps of providing a fluorescent entity capable of indicating the presence of the nucleic acid and capable of providing a signal related to the quantity of the nucleic acid, initially amplifying the nucleic acid through a set number of amplification cycles in the presence of the fluorescent entity, measuring fluorescence intensity of the fluorescent entity at each of the amplification cycles to produce a fluorescent value for each cycle related to the quantity of the nucleic acid present at each cycle, generating a fluorescence-verses-amplification-cycle plot wherein the fluorescent values are recorded for each amplification cycle, calculating slopes of segments of the fluorescence-verses-amplification-cycle plot using a plurality of the fluorescent values, using the slopes to identify amplification cycles for use in establishing a baseline fluorescence region, ascertaining whether a positive result is indicated by determining whether the fluorescence value during any of the of amplification cycles is outside the baseline fluorescence region, and continuing amplification through additional amplification cycles and repeating the measuring, determining, and ascertaining steps after each additional amplification cycle until either the positive result is obtained or a maximum cycle number is reached.

10. The method of claim 9 further comprising the steps of performing additional amplification cycles after the positive result is obtained, and analyzing the nucleic acid for additional information.

11. The method of claim 9 wherein the nucleic acid is further analyzed to determine the presence of a particular allele.

12. The method of claim 9 wherein the measured fluorescence is further analyzed to determine initial concentration.

13. An automated method for determining the presence of a nucleic acid comprising the steps of placing a sample into a container containing a fluorescent entity capable of indicating the presence of the nucleic acid and capable of providing a signal related to the quantity of the nucleic acid, placing the container into a device for amplifying the nucleic acid through a plurality of amplification cycles in the presence of the fluorescent entity, measuring fluorescence intensity of the fluorescent entity at each of the plurality of amplification cycles to produce a fluorescent value for each cycle related to the quantity of the nucleic acid present at each cycle, generating a fluorescence-verses-amplification-cycle plot wherein the fluorescent values are recorded for each amplification cycle, calculating slopes of segments of the fluorescence-verses-amplification-cycle plot using a plurality of the fluorescent values, using the segment slopes of the fluorescence-verses-amplification-cycle plot to establish a baseline fluorescence region by generating a slope value for each of a plurality of the amplification cycles, and establishing the baseline fluorescence region comprising an interval of cycles that includes the amplification cycle with the slope value having an absolute value closest to zero, and outputting a positive result if the fluorescence value of a selected amplification cycle is outside the baseline fluorescence region.

14. The method of claim 8 wherein the fluorescent entity comprises a FRET oligonucleotide pair configured to provide increased fluorescence signal in the presence of increased amounts of the amplified nucleic acid and the ascertaining step includes determining whether the fluorescence value of the selected amplification cycle is greater than the baseline fluorescence region.

15. The method of claim 1 wherein the fluorescence intensity is measured during primer extension.

16. The method of claim 1 wherein the fluorescence intensity is measured once each cycle subsequent to primer extension.

17. The method of claim 6 wherein the fluorescence intensity is measured during a probe annealing phase.

18. A method for determining the presence of a nucleic acid comprising the steps of providing a fluorescent entity capable of indicating the presence of the nucleic acid and capable of providing a fluorescence intensity related to the quantity of the nucleic acid, amplifying the nucleic acid through a plurality of amplification cycles in the presence of the fluorescent entity, measuring the fluorescence intensity of the fluorescent entity at each of the plurality of amplification cycles to produce a fluorescent value for each cycle related to the quantity of the nucleic acid present at each cycle, generating an array wherein the fluorescent values are recorded for each amplification cycle, calculating first derivative values of a plurality windows of the array using a plurality of the fluorescent values, establishing a baseline confidence interval using an interval of windows that includes the window having a first derivative absolute value closest to zero, and ascertaining whether the fluorescence value produced during a selected amplification cycle is outside the baseline confidence interval.

19. The method of claim 18 further comprising the steps of calculating second derivative values of windows of the array, and determining that the array is well-behaved, and wherein the plurality of windows are the windows prior to a cutoff cycle.

20. The method of claim 11 wherein the selected amplification cycle is the cycle having the fluorescent value farthest from the baseline.

21. The method of claim 18 further comprising the steps of calculating second derivative values of windows of the array, and determining that the array is not well-behaved, and wherein the plurality of windows include all amplification cycles.

22. The method of claim 21 in wherein the selected amplification cycle is the last cycle.

23. A method for determining the presence of a nucleic acid comprising the steps of providing a fluorescent entity capable of indicating the presence of the nucleic acid and capable of providing a signal related to the quantity of the nucleic acid, amplifying the nucleic acid through a plurality of amplification cycles in the presence of the fluorescent entity, measuring fluorescence intensity of the fluorescent entity at each of the plurality of amplification cycles to produce a fluorescent value for each cycle related to the quantity of the nucleic acid present at each cycle, generating a well-behaved fluorescence-verses-amplification-cycle plot wherein the fluorescent values are recorded for each amplification cycle, determining a cutoff cycle, calculating slopes of segments of the fluorescence-verses-amplification-cycle plot using a plurality of the fluorescent values, using the slopes of segments to assign slope values for a plurality of the amplification cycles prior to the cutoff cycle, choosing the fluorescent intensity measurement of the amplification cycle with the slope value having and absolute value closest to zero for establishing a baseline fluorescence region, and ascertaining whether the fluorescence value during a selected amplification cycle is outside the baseline fluorescence region.

24. The method of claim 23 wherein the cutoff cycle is selected from the group consisting of a maximum second derivative, a maximum first derivative, and a minimum second derivative of the fluorescence-verses-amplification-cycle plot.

* * * * *